(12) United States Patent
Harada (10) Patent No.: US 11,396,566 B2
(45) Date of Patent: Jul. 26, 2022

(54) FLUORESCENT RESIN PARTICLES AND USE THEREOF

(71) Applicant: SEKISUI KASEI CO., LTD., Osaka (JP)

(72) Inventor: Ryosuke Harada, Osaka (JP)

(73) Assignee: SEKISUI KASEI CO., LTD., Osaka (JP)

( * ) Notice: Subject to any disclaimer, the term of this patent is extended or adjusted under 35 U.S.C. 154(b) by 790 days.

(21) Appl. No.: 16/337,493

(22) PCT Filed: Sep. 29, 2017

(86) PCT No.: PCT/JP2017/035604
§ 371 (c)(1),
(2) Date: Mar. 28, 2019

(87) PCT Pub. No.: WO2018/062522
PCT Pub. Date: Apr. 5, 2018

(65) Prior Publication Data
US 2019/0284320 A1    Sep. 19, 2019

(30) Foreign Application Priority Data
Sep. 30, 2016  (JP) .............................. JP2016-194503

(51) Int. Cl.
| | | |
|---|---|---|
| *C08F 212/12* | (2006.01) | |
| *C08F 212/08* | (2006.01) | |
| *C08F 218/10* | (2006.01) | |
| *C08F 220/68* | (2006.01) | |
| *C09B 11/24* | (2006.01) | |
| *C09B 67/00* | (2006.01) | |
| *C09D 5/22* | (2006.01) | |
| *C09D 125/14* | (2006.01) | |
| *C09D 125/16* | (2006.01) | |
| *C09D 131/02* | (2006.01) | |
| *C09D 133/08* | (2006.01) | |
| *C08F 220/10* | (2006.01) | |
| *C08F 2/44* | (2006.01) | |
| *C09B 67/46* | (2006.01) | |
| *G01N 33/533* | (2006.01) | |

(52) U.S. Cl.
CPC .............. *C08F 212/12* (2013.01); *C08F 2/44* (2013.01); *C08F 212/08* (2013.01); *C08F 218/10* (2013.01); *C08F 220/10* (2013.01); *C08F 220/68* (2013.01); *C09B 11/24* (2013.01); *C09B 67/0084* (2013.01); *C09D 5/22* (2013.01); *C09D 125/14* (2013.01); *C09D 125/16* (2013.01); *C09D 131/02* (2013.01); *C09D 133/08* (2013.01); *G01N 33/533* (2013.01)

(58) Field of Classification Search
CPC .... C08F 212/12; C08F 212/08; C08F 218/10; C08F 220/68; C08F 220/10; C08F 2/44; C09B 11/24; C09B 67/0084; C09D 5/22; C09D 125/14; C09D 125/16; C09D 131/02; C09D 133/08
USPC ....................................................... 252/301.35
See application file for complete search history.

(56) References Cited

U.S. PATENT DOCUMENTS

| | | | | |
|---|---|---|---|---|
| 5,435,937 A | * | 7/1995 | Bell ........................ | C09K 11/04 556/26 |
| 5,658,494 A | * | 8/1997 | Bell ........................ | C09K 11/04 556/19 |
| 6,727,318 B1 | | 4/2004 | Mathauer et al. | |
| 8,222,313 B2 | * | 7/2012 | Iftime .................... | C09D 11/101 522/74 |
| 8,546,502 B2 | * | 10/2013 | Shimanaka ........... | C09B 69/108 526/204 |
| 2005/0075453 A1 | | 4/2005 | Mathauer et al. | |
| 2010/0086701 A1 | * | 4/2010 | Iftime .................... | C09D 11/32 524/556 |
| 2011/0112242 A1 | * | 5/2011 | Shimanaka ............... | C08F 2/38 526/204 |
| 2016/0375143 A1 | * | 12/2016 | Gunatillake .............. | A61P 3/10 514/44 A |

FOREIGN PATENT DOCUMENTS

| | | | | |
|---|---|---|---|---|
| DE | 19805121 | | 8/1999 | |
| JP | 5-133970 | | 5/1993 | |
| JP | 2003-313545 | | 11/2003 | |
| JP | 2006-265401 | | 10/2006 | |
| JP | 2010-229219 | | 10/2010 | |
| JP | 2014034588 A | * | 2/2014 | |
| JP | 2015120814 A | * | 7/2015 | |
| WO | WO-2015194611 A1 | * | 12/2015 | ............. B32B 25/08 |

OTHER PUBLICATIONS

Notice of Reasons for Refusal dated Jun. 30, 2020 in corresponding Japanese Patent Application No. 2018-542956, with English translation.

Extended European Search Report dated Mar. 6, 2020 in European Patent Application No. 17856469.6.

* cited by examiner

*Primary Examiner* — Michael M. Bernshteyn
(74) *Attorney, Agent, or Firm* — Wenderoth, Lind & Ponack, L.L.P.

(57) ABSTRACT

Fluorescent resin particles which comprise a water-soluble fluorescent dye and a polymer made from a monomer mixture.

12 Claims, 2 Drawing Sheets

FLUORESCENT RESIN PARTICLES AND USE THEREOF

TECHNICAL FIELD

The present invention relates to fluorescent resin particles containing a water-soluble fluorescent dye and a polymer made from a vinyl-based monomer, and use of such fluorescent resin particles (a dispersion and a resin composition).

BACKGROUND ART

Currently, fluorescent particles that develop fluorescence are widely used in various fields. Above all, fluorescent particles play an important role as tracer particles for a fluid visualization system, reference particles for quality control in flow cytometry, and catalytic supports for an immunodiagnostic agent.

For observations of a fluid flow in a chemical plant, a fluid flow in a nuclear reactor core (a gentle flow of fluid by convection), cavitation by screw rotations in a ship or submarine, or other similar observations, it is desirable to bring the scale of the test closer to the full scale. In such a large-scale fluid measurement, fluorescence needs to be noticeable enough to be captured by a camera.

PTL 1 discloses a method for producing vinyl-based polymer particles by dispersing a vinyl-based monomer and a water-soluble fluorescent dye in an aqueous medium and polymerizing the vinyl-based monomer to provide vinyl-based polymer particles containing the water-soluble fluorescent dye. This polymerization is emulsion polymerization in the presence of a surfactant and a polymerization initiator. As the vinyl-based monomer, the emulsion polymerization employs a vinyl-based monomer containing a carboxyl group and another vinyl-based monomer containing a functional group that can bond to the carboxyl group in the vinyl-based monomer. For the emulsion polymerization, these vinyl-based monomers are dispersed in the aqueous medium.

CITATION LIST

Patent Literature

[PTL 1] JP 2010-229219 A

SUMMARY OF INVENTION

Technical Problem

In view of the above-mentioned conventional vinyl-based polymer particles containing the water-soluble fluorescent dye, the inventor of the present application made large-diameter particles having a similar composition, and then found that the obtained particles contained a large amount of emulsion (microparticles). When the inventor of the present application applied such particles to a large-scale fluid measurement, the emulsion separated from the surfaces of the fluorescent resin particles and blurred an image of the fluid flow derived from the fluorescent resin particles in the intended particle size. From this test, the inventor found that such particles are not suitable for observation of a fluid flow, and also found that these particles do not follow the fluid flow very well.

The present invention is made in order to solve the above conventional problems. An object of the present invention is to provide fluorescent resin particles that can follow a fluid flow better and can facilitate observation of the fluid flow when applied to fluid visualization, and to provide a dispersion and a resin composition using such fluorescent resin particles.

Solution to Problem

Fluorescent resin particles according to the present invention contain a water-soluble fluorescent dye and a polymer made from a monomer mixture. The monomer mixture is a mixture of 20% to 80% by mass of a first vinyl-based monomer and 80% to 20% by mass of a second vinyl-based monomer. The first vinyl-based monomer is at least one monofunctional vinyl-based monomer selected from the group consisting of a styrene derivative having an alkyl group with 3 to 30 carbon atoms, a (meth)acrylic acid ester having an alkyl group with 10 to 30 carbon atoms, and a vinyl ester having an alkyl group with 10 to 30 carbon atoms. The second vinyl-based monomer contains at least one monofunctional vinyl-based monomer selected from the group consisting of styrene, a styrene derivative having an alkyl group with two carbon atoms or less, a (meth)acrylic acid ester having an alkyl group with nine carbon atoms or less, and a vinyl ester having an alkyl group with nine carbon atoms or less.

In the above configuration, at least one monofunctional vinyl-based monomer selected from the group consisting of a styrene derivative having an alkyl group with 3 to 30 carbon atoms, a (meth)acrylic acid ester having an alkyl group with 10 to 30 carbon atoms, and a vinyl ester having an alkyl group with 10 to 30 carbon atoms is added in a suitable amount to the monomer mixture that contains at least one monofunctional vinyl-based monomer selected from the group consisting of styrene, a styrene derivative having an alkyl group with two carbon atoms or less, a (meth)acrylic acid ester having an alkyl group with nine carbon atoms or less, and a vinyl ester having an alkyl group with nine carbon atoms or less. As a result, even the fluorescent resin particles having a relatively large particle size can follow a fluid flow better. Therefore, the fluorescent resin particles according to the present invention are suitable for use in large-scale fluid visualization.

In the above configuration, at least one monofunctional vinyl-based monomer having a low solubility in water and selected from the group consisting of a styrene derivative having an alkyl group with 3 to 30 carbon atoms, a (meth)acrylic acid ester having an alkyl group with 10 to 30 carbon atoms, and a vinyl ester having an alkyl group with 10 to 30 carbon atoms is added to the monomer mixture that contains at least one monofunctional vinyl-based monomer selected from the group consisting of styrene, a styrene derivative having an alkyl group with two carbon atoms or less, a (meth)acrylic acid ester having an alkyl group with nine carbon atoms or less, and a vinyl ester having an alkyl group with nine carbon atoms or less. When the fluorescent resin particles are produced, for example, by suspension polymerization in an aqueous medium, this configuration inhibits generation of emulsion (microparticles) due to emulsion polymerization in the aqueous phase. Eventually, in fluid visualization, such fluorescent resin particles prevent separation of the emulsion from the surfaces of the fluorescent resin particles, prevent blurring of an image of a fluid flow derived from the fluorescent resin particles in the intended particle size, and thereby facilitate observation of the fluid flow. In this application document, the term "(meth)acrylic acid" means acrylic acid and/or methacrylic acid, and the term "(meth)acrylate" means acrylate and/or methacrylate.

A dispersion according to the present invention contains the fluorescent resin particles of the present invention. When the dispersion of the present invention that contains the fluorescent resin particles of the present invention is employed in fluid visualization, the fluorescent resin particles can follow a fluid flow better and can facilitate observation of the fluid flow.

A resin composition according to the present invention contains the fluorescent resin particles of the present invention and a binder resin. Since the resin composition of the present invention contains the fluorescent resin particles of the present invention that are less likely to settle out in the fluid, the fluorescent resin particles are uniformly dispersed in the binder resin.

Advantageous Effects of Invention

The present invention can provide fluorescent resin particles that can follow a fluid flow better and can facilitate observation of the fluid flow when applied to fluid visualization. The present invention can also provide a dispersion and a resin composition using such fluorescent resin particles.

DESCRIPTION OF EMBODIMENTS

The present invention is hereinafter described in detail.
<Fluorescent Resin Particles>

The fluorescent resin particles according to the present invention contain a water-soluble fluorescent dye and a polymer made from a monomer mixture. The monomer mixture is a mixture of 20% to 80% by mass of a first vinyl-based monomer and 80% to 20% by mass of a second vinyl-based monomer. The first vinyl-based monomer is at least one monofunctional vinyl-based monomer selected from the group consisting of a styrene derivative having an alkyl group with 3 to 30 carbon atoms, a (meth)acrylic acid ester having an alkyl group with 10 to 30 carbon atoms, and a vinyl ester having an alkyl group with 10 to 30 carbon atoms. The second vinyl-based monomer contains at least one monofunctional vinyl-based monomer selected from the group consisting of styrene, a styrene derivative having an alkyl group with two carbon atoms or less, a (meth)acrylic acid ester having an alkyl group with nine carbon atoms or less, and a vinyl ester having an alkyl group with nine carbon atoms or less.

The first vinyl-based monomer is at least one monofunctional vinyl-based monomer selected from the group consisting of styrene derivatives each having an alkyl group with 3 to 30 carbon atoms, (meth)acrylic acid esters each having an alkyl group with 10 to 30 carbon atoms, and vinyl esters each having an alkyl group with 10 to 30 carbon atoms. This monofunctional vinyl-based monomer is relatively hydrophobic. In this context, "a vinyl-based monomer" means a compound having at least one ethylenic unsaturated group, and "a monofunctional vinyl-based monomer" means a compound having a single ethylenic unsaturated group.

The styrene derivatives each having an alkyl group with 3 to 30 carbon atoms include, for example, p-n-butylstyrene, p-tert-butylstyrene, p-n-hexylstyrene, p-n-octylstyrene, p-n-nonylstyrene, p-n-decylstyrene, p-n-dodecylstyrene, etc. The (meth)acrylic acid esters each having an alkyl group with 10 to 30 carbon atoms include, for example, dodecyl (meth)acrylate, stearyl (meth)acrylate, isostearyl (meth) acrylate, hexadecyl (meth)acrylate, octadecyl (meth)acrylate, icosyl (meth)acrylate, etc. The vinyl esters each having an alkyl group with 10 to 30 carbon atoms include, for example, vinyl laurate, vinyl myristate, vinyl palmitate, vinyl stearate, etc. Preferably, the first vinyl-based monomer is any of the styrene derivatives each having an alkyl group with 3 to 30 carbon atoms because the resulting fluorescent resin particles can follow a fluid flow better.

In the monomer mixture, the content of the first vinyl-based monomer simply needs to be 20% to 80% by mass, but is preferably 30% to 80% by mass, and is more preferably 40% to 75% by mass. The resulting fluorescent resin particles can follow a fluid flow even better.

The second vinyl-based monomer contains at least one monofunctional vinyl-based monomer (hereinafter called "specified monofunctional vinyl-based monomer") selected from the group consisting of styrene, styrene derivatives each having an alkyl group with two carbon atoms or less, (meth)acrylic acid esters each having an alkyl group with nine carbon atoms or less, and vinyl esters each having an alkyl group with nine carbon atoms or less. The styrene derivatives having an alkyl group with two carbon atoms or less include, for example, o-methylstyrene, m-methylstyrene, p-methylstyrene, p-ethylstyrene, 2,4-dimethylstyrene, n-methoxystyrene, etc. The (meth)acrylic acid esters each having an alkyl group with nine carbon atoms or less include, for example, methyl (meth)acrylate, ethyl (meth) acrylate, propyl (meth)acrylate, n-butyl (meth)acrylate, isobutyl (meth)acrylate, n-octyl (meth)acrylate, 2-ethylhexyl (meth)acrylate, diethylaminomethyl (meth) acrylate, diethylaminoethyl (meth) acrylate, 2-methacryloyloxyethyl succinate, 2-methacryloyloxyethyl phthalate, 2-methacryloyloxyethyl hexahydrophthalate, etc. The vinyl esters each having an alkyl group with nine carbon atoms or less include, for example, vinyl acetate, vinyl propionate, vinyl butyrate, etc. Preferably, the specified monofunctional vinyl-based monomer is any of styrene and the styrene derivatives each having an alkyl group with two carbon atoms or less because the resulting fluorescent resin particles can follow a fluid flow better.

In the monomer mixture, the content of the specified monofunctional vinyl-based monomer simply needs to be 20% to 80% by mass, but is preferably 30% to 80% by mass, and is more preferably 40% to 75% by mass. The resulting fluorescent resin particles can follow a fluid flow even better.

Preferably, the second vinyl-based monomer contains a monofunctional vinyl-based monomer which has a carboxy group and whose solubility at 20° C. is 50 g or less per 100 ml water. The monofunctional vinyl-based monomer which has a carboxy group and whose solubility at 20° C. is 50 g or less per 100 ml water is relatively hydrophobic. During polymerization, the carboxy group bonds to a basic site of a molecule in a water-soluble fluorescent dye (for example, an amino group in a rhodamine dye), thereby making the water-soluble fluorescent dye hydrophobic and facilitating its uniform dissolution in the monomer mixture. As a result, the water-soluble fluorescent dye can be uniformly distributed in the fluorescent resin particles, and the resulting fluorescent resin particles can produce fluorescence uniformly among themselves. For this vinyl-based monomer having a carboxy group, the solubility at 20° C. per 100 ml water is preferably 30 g or less, and more preferably 10 g or less.

The vinyl-based monomer which has a carboxy group and whose solubility at 20° C. is 50 g or less per 100 ml water (hereinafter called "carboxy group-containing monofunctional vinyl-based monomer") may be, for example, a (meth) acrylic acid derivative such as 2-methacryloyloxyethyl succinate [solubility 1.9 g], 2-methacryloyloxyethyl phthalate, or 2-methacryloyloxyethyl hexahydrophthalate. These derivatives may be used alone or in combination.

In the monomer mixture, the content of the carboxy group-containing monofunctional vinyl-based monomer is preferably 2% to 30% by mass, and more preferably 4% to 25% by mass. The resulting fluorescent resin particles can produce fluorescence more uniformly among themselves.

The fluorescent resin particles may further contain a carboxylic acid which is free of an ethylenic unsaturated group and whose solubility at 20° C. is 50 g or less per 100 ml water. The effect achieved by such fluorescent resin particles is equivalent to the one achieved by the fluorescent resin particles in which the second vinyl-based monomer contains a carboxy group-containing monofunctional vinyl-based monomer. To be specific, the carboxylic acid which is free of an ethylenic unsaturated group and whose solubility at 20° C. is 50 g or less per 100 ml water is relatively hydrophobic. During polymerization, the carboxy group bonds to a basic site of a molecule in a water-soluble fluorescent dye (for example, an amino group in a rhodamine dye), thereby making the water-soluble fluorescent dye hydrophobic and facilitating its uniform dissolution in the monomer mixture. As a result, the water-soluble fluorescent dye can be uniformly distributed in the fluorescent resin particles, and the resulting fluorescent resin particles can produce fluorescence uniformly among themselves. For this carboxylic acid free of an ethylenic unsaturated group, the solubility at 20° C. per 100 ml water is preferably 30 g or less, and more preferably 10 g or less.

The carboxylic acid which is free of an ethylenic unsaturated group and whose solubility at 20° C. is 50 g or less per 100 ml water may be, for example, octanoic acid, heptanoic acid, hexanoic acid, or the like. These acids may be used alone or in combination.

In the fluorescent resin particles, the content of the carboxylic acid which is free of an ethylenic unsaturated group and whose solubility at 20° C. is 50 g or less per 100 ml water is preferably 2% to 30% by mass, and more preferably 4% to 25% by mass. The resulting fluorescent resin particles can produce fluorescence more uniformly among themselves.

The second vinyl-based monomer may also contain a polyfunctional vinyl-based monomer. The polyfunctional vinyl-based monomer is a compound having two or more ethylenic unsaturated groups. The polyfunctional vinyl-based monomers may be any of alkylene glycol di(meth) acrylates ($C_{2-4}$ alkylenes are preferable) such as divinylbenzene, and ethylene glycol dimethacrylate.

The second vinyl-based monomer may also contain an additional monofunctional vinyl-based monomer. Examples of the additional monofunctional vinyl-based monomer include styrene derivatives such as p-phenylstyrene, p-chlorostyrene, and 3,4-dichlorostyrene; vinyl halides such as vinyl chloride, vinylidene chloride, vinyl bromide, and vinyl fluoride; vinyl esters such as vinyl benzoate; a-methylene aliphatic monocarboxylic acid esters such as 2-chloroethyl (meth)acrylate, and phenyl (meth)acrylate; (meth)acrylic acid derivatives such as (meth)acrylonitrile and (meth)acrylamide; etc.

The additional monofunctional vinyl-based monomer may further be any of the following: vinyl ethers such as vinyl methyl ether, vinyl ethyl ether, and vinyl isobutyl ether; vinyl ketones such as vinyl methyl ketone, vinyl hexyl ketone, and methyl isopropenyl ketone; N-vinyl compounds such as N-vinylpyrrole, N-vinylcarbazole, N-vinylindole, and N-vinylpyrrolidone; and vinylnaphthalene.

The water-soluble fluorescent dye, which simply needs to be soluble in the monomer mixture substantially uniformly, is not particularly limited. The water-soluble fluorescent dye may be any of the following: rhodamine dyes such as Rhodamine B, Rhodamine 6G, and Rhodamine 640; stilbene-based dyes; methylene blue; fluorescein-based dyes (fluorescein derivatives) such as fluorescein, uranine, and erythrosine; etc. Above all, rhodamine dyes such as Rhodamine B, Rhodamine 6G, and Rhodamine 640, or fluorescein-based dyes such as fluorescein, uranine, and erythrosine are suitable for the water-soluble fluorescent dye.

The amount of water-soluble fluorescent dye, which may be affected by the species of the water-soluble fluorescent dye or by other conditions, is preferably in the range of 0.005 to 20 parts by mass, and more preferably in the range of 0.01 to 10 parts by mass, relative to 100 parts by mass of the above-mentioned polymer. If the amount of water-soluble fluorescent dye is less than 0.005 parts by mass, the fluorescent resin particles may not have sufficient fluorescence-emitting property. If the amount of water-soluble fluorescent dye is more than 20 parts by mass, the expected effect is unlikely to be proportionate to the increased amount. In the case where the fluorescent resin particles are produced by polymerization of the monomer mixture in the presence of the water-soluble fluorescent dye, more than 20 parts by mass of the water-soluble fluorescent dye may cause deposition of the undissolved matter and/or may inhibit polymerization of the monomer mixture.

Preferably, the fluorescent resin particles further contain a surfactant. The surfactant makes the fluorescent resin particles hydrophilic and facilitates their dispersion in water. In fluid visualization, such fluorescent resin particles facilitate observation of a fluid flow.

The surfactant may be added during or after the polymerization for production of the fluorescent resin particles. The surfactant, which may be anionic, cationic, non-ionic, or amphoteric, is preferably non-ionic.

The anionic surfactant may be any of the known anionic surfactants including fatty acid salts, sulfates, sulfonates, etc. Examples of the anionic surfactant are fatty acid soaps such as sodium oleate, and castor oil potassium soap; alkyl sulfates such as sodium lauryl sulfate, and ammonium lauryl sulfate; alkyl benzene sulfonates such as sodium dodecylbenzene sulfonate; dialkyl sulfosuccinates such as alkyl naphthalene sulfonates, alkane sulfonates, di(2-ethylhexyl) sulfosuccinate (sodium salt), and dioctyl sulfosuccinate (sodium salt); alkenyl succinates (dipotassium salts); alkyl phosphates; naphthalene sulfonate formalin condensates; polyoxyethylene alkyl phenyl ether sulfates; polyoxyethylene alkyl ether sulfates such as sodium polyoxyethylene lauryl ether sulfates; polyoxyethylene alkyl sulfate esters; polyoxyethylene styrenated phenyl ether sulfates; etc. These anionic surfactants may be used alone or in combination.

The non-ionic surfactant may be any of the known non-ionic surfactants including esters, ethers, ester-ethers, etc. Examples of the non-ionic surfactant are polyoxyethylene alkyl ethers such as polyoxyethylene tridecyl ether;

polyoxyethylene alkyl phenyl ethers such as polyoxyethylene octyl phenyl ether; polyoxyalkylene alkyl ethers such as polyoxyethylene styrenated phenyl ether, and polyoxyalkylene tridecyl ethers in which the alkylene group have three or more carbon atoms each; polyoxyethylene sorbitan fatty acid esters such as polyoxyethylene fatty acid ester, sorbitan fatty acid ester, and polyoxyethylene sorbitan monolaurate; polyoxyethylene alkylamines, glycerin fatty acid ester, oxyethylene-oxypropylene block polymer, etc. These non-ionic surfactants may be used alone or in combination.

The cationic surfactant may be any of the known cationic surfactants including amine salts, quaternary ammonium salts, etc. In terms of handleability, water-soluble cationic surfactants are advantageous. Specific examples of the cationic surfactant are alkylamine salts such as laurylamine acetate, and stearylamine acetate; alkyl trimethyl ammonium chlorides such as lauryl trimethyl ammonium chloride, hexadecyl trimethyl ammonium chloride, cocoyl trimethyl ammonium chloride, and dodecyl trimethyl ammonium chloride; alkyl dimethyl benzyl chlorides such as hexadecyl dimethyl benzyl ammonium chloride, and lauryl dimethyl benzyl ammonium chloride; etc. These cationic surfactants may be used alone or in combination.

Examples of the amphoteric surfactant are lauryl dimethylamine oxide, phosphate surfactants, phosphite surfactants, etc. These amphoteric surfactants may be used alone or in combination.

The above-mentioned surfactants may be used alone or in combination. The solubility of the surfactant in 25° C. water is preferably 0.3 g/100 ml or more, and more preferably 0.5 g/100 ml or more. The surfactant having a solubility of less than 0.3 g/100 ml may not ensure a sufficient effect of hydrophilizing the fluorescent resin particles. Among these surfactants, one having a polyoxyethylene chain is preferable because it readily adheres to the surface of the polymer.

In the fluorescent resin particles, the content of the surfactant is in the range of 0.01 to 0.5 parts by weight relative to 100 parts by weight of the polymer. A surfactant content below this range may not be able to ensure a sufficient effect of hydrophilizing the fluorescent resin particles. A surfactant content above this range is uneconomical.

The fluorescent resin particles may further contain other additives, without sacrificing the effect of the present invention.

Examples of such additives are coloring components (coloring agents) except the water-soluble fluorescent dye, light stabilizers, UV absorbers, heat stabilizers, leveling agents, antistatics, etc.

The emulsion content index value for the fluorescent resin particles is preferably 100 NTU or less, more preferably 70 NTU or less, and further preferably 40 NTU or less. The emulsion content index value is measured as a turbidity of a filtrate of a dispersion in which the fluorescent resin particles are dispersed in water, with the proviso that the amount of water is three times as much as the mass of the fluorescent resin particles, and that the dispersion is filtered through "Qualitative Filter Paper No. 101" (manufactured by Toyo Roshi Kaisha, Ltd.) to give the filtrate. In fluid visualization, such fluorescent resin particles prevent separation of the emulsion from the surfaces of the fluorescent resin particles, prevent blurring of an image of a fluid flow derived from the fluorescent resin particles in the intended particle size, and thereby facilitate observation of the fluid flow. An example of the method for measuring the emulsion content index value will be described in the section of Examples.

The volume-average particle size of the fluorescent resin particles is preferably between 30 and 500 μm, and more preferably between 30 and 200 μm. When applied to large-scale fluid visualization for visualizing a fluid flow in a chemical plant, a fluid flow in a nuclear reactor, a fluid flow created by screw rotations in a ship or submarine, such fluorescent resin particles facilitate observation of the fluid flow.

The coefficient of variation in volume-based particle size of the fluorescent resin particles is preferably 32% or less, and more preferably 25% or less. Such fluorescent resin particles can follow a fluid flow better.

The true specific gravity of the fluorescent resin particles is preferably between 0.95 and 1.05. When the fluid to be visualized is water, such fluorescent resin particles are less likely to settle out or suspend in the water.

<Method for Producing the Fluorescent Resin Particles>

The method for producing the fluorescent resin particles according to the present invention is not particularly limited. The fluorescent resin particles may be produced by polymerizing the monomer mixture by various polymerization processes (emulsion polymerization, dispersion polymerization, suspension polymerization, seeded polymerization, etc.) in the presence of the water-soluble fluorescent dye. Among such polymerization processes, suspension polymerization is preferable because it can easily produce fluorescent resin particles having a volume-average particle size of 30 to 500 μm by allowing a mixture of the monomer mixture and the water-soluble fluorescent dye to suspend and polymerize in an aqueous medium.

The aqueous medium for suspension polymerization may be water, or a mixture of water and a water-soluble organic solvent (for example, a lower alcohol with five carbon atoms or less).

In the suspension polymerization, where necessary, a polymerization initiator may be added to the mixture containing the monomer mixture and the water-soluble fluorescent dye. Examples of the polymerization initiator include oil-soluble peroxides such as benzoyl peroxide, lauroyl peroxide, octanoyl peroxide, ortho-chlorobenzoyl peroxide, methyl ethyl ketone peroxide, diisopropyl peroxydicarbonate, cumene hydroperoxide, and t-butylhydroperoxide; oil-soluble azo compounds such as 2,2'-azobisisobutyronitrile, and 2,2'-azobis(2,4-dimethylvaleronitrile). These polymerization initiators may be used alone or in combination. The sufficient amount of polymerization initiator is merely about 0.1 to 1 part by mass relative to 100 parts by mass of the monomer mixture.

Where necessary, the suspension polymerization may proceed in the presence of a dispersant and/or a surfactant. Examples of the dispersant include poorly water-soluble inorganic salts such as calcium phosphate, and magnesium pyrophosphate; water-soluble polymers such as polyvinyl alcohol, methylcellulose, and polyvinylpyrrolidone; etc.

Examples of the surfactant include anionic surfactants such as sodium oleate, sodium lauryl sulfate, sodium dodecylbenzene sulfonate, alkyl naphthalene sulfonates, and alkyl phosphate ester salts; non-ionic surfactants such as polyoxyethylene alkyl ethers, polyoxyethylene alkyl phenyl ethers, polyoxyethylene fatty acid esters, sorbitan fatty acid esters, polyoxysorbitan fatty acid esters, polyoxyethylene alkylamines, glycerin fatty acid esters; amphoteric surfactants such as lauryl dimethylamine oxide; etc.

These dispersants and the surfactants may be used alone or in combination. Above all, it is preferable to use both a surfactant and a dispersant together, to choose a water-soluble polymer as the dispersant, and to add the surfactant not at the start of the polymerization but after a first-stage heating (in order to prevent flocculation after the first-stage heating). Use of a water-soluble polymer as the dispersant and absence of the surfactant at the start of the polymerization can further reduce the emulsion content in the fluorescent resin particles.

The amount of dispersant is preferably 0.5 to 10 parts by mass relative to 100 parts by mass of the monomer mixture. The amount of surfactant is preferably 0.01 to 0.2 parts by mass relative to 100 parts by mass of the aqueous medium.

For suspension polymerization of the monomer mixture, the mixture containing the monomer mixture and the water-soluble fluorescent dye preferably contains an acidic modified organophosphate compound. When the mixture is caused to suspend in the aqueous medium, the acidic modified organophosphate compound in the mixture can prevent migration of the water-soluble fluorescent dye and the unreacted monomer to the aqueous phase and enables generation of stable fine oil droplets of the mixture.

Examples of the acidic modified organophosphate compound include phosphorous acid monoesters, phosphorous acid diesters, phosphoric acid monoesters, and phosphoric acid diesters. Such phosphorous acid monoesters, phosphorous acid diesters, phosphoric acid monoesters, and phosphoric acid diesters are not particularly limited, and include lauryl phosphate, polyoxyethylene(1) lauryl ether phosphate, dipolyoxyethylene(2) alkyl ether phosphates, dipolyoxyethylene(4) alkyl ether phosphates, dipolyoxyethylene(6) alkyl ether phosphates, dipolyoxyethylene(8) alkyl ether phosphates, dipolyoxyether(4) nonylphenyl ether phosphate, caprolactone ethoxylated phosphate dimethacrylate, 2-methacryloyloxyethyl acid phosphate, etc. Among these compounds, lauryl phosphate, or caprolactone ethoxylated phosphate dimethacrylate is preferable.

The acidic modified organophosphate compound is added preferably in an amount of 0.01 to 5 parts by mass, and more preferably 0.01 to 3 parts by mass, relative to 100 parts by mass of the monomer mixture.

For suspension polymerization, an oil phase containing the monomer mixture is prepared and dispersed in an aqueous phase containing an aqueous medium. The aqueous phase with the dispersed oil phase is heated to start the polymerization. The polymerization initiator, if required, is mixed with the monomer mixture during the preparation of the oil phase. The dispersant and/or the surfactant, if required, is/are mixed with the aqueous medium during the preparation of the aqueous phase. The volume-average particle size of the fluorescent resin particles can be suitably controlled by adjustment of the proportion of the oil phase to the aqueous phase, the amount of dispersant and surfactant, the stirring condition, and the dispersion condition.

The oil phase may be dispersed in the aqueous phase in various manners: for example, by adding the oil phase directly to the aqueous phase, and utilizing the stirring force of propeller blades or the like to disperse droplets of the oil phase into the aqueous phase; by adding the oil phase directly to the aqueous phase, and utilizing the shear force of a homomixer that is a high-shear disperser equipped with a rotor and a stator to disperse the oil phase in the aqueous phase; or by adding the oil phase directly to the aqueous phase, and using an ultrasonic disperser or the like to disperse the oil phase in the aqueous phase. Considering the uniformity of the particle size of the obtained fluorescent resin particles, it is preferable to add the oil phase directly to the aqueous phase and to use a high-pressure disperser such as a microfluidizer or a Nanomizer®. In this case, droplets of the mixture are caused to collide with each other or with the wall of the disperser, so that droplets of the oil phase can be dispersed into the aqueous phase. It is also preferable to force the oil phase into the aqueous phase through an MPG (microporous glass) porous membrane.

A preferable polymerization temperature is approximately from 40° C. to 90° C. Preferably, this polymerization temperature is kept approximately for 0.1 to 10 hours. The polymerization reaction may be conducted in an inert gas atmosphere (such as a nitrogen atmosphere) that is inactive against a reactant (the oil phase) in the polymerization reaction system. If the boiling point of the monomer mixture is around or lower than the polymerization temperature, suspension polymerization is conducted hermetically or under elevated pressure in a pressure-resistant polymerization facility such as an autoclave so as to prevent volatilization of the vinyl-based monomer.

After completion of the polymerization reaction, the fluorescent resin particles can be obtained through an optional treatment such as decomposition and removal of a poorly water-soluble inorganic salt with use of an acid or the like, dehydration by filtration or the like, washing, drying, pulverization, and classification. To obtain fluorescent resin particles with a small emulsion content index value (e.g., 100 NTU or less), an emulsion (microparticles) generated during the polymerization is removed by classification (e.g., air classification), filtration, etc.

To produce fluorescent resin particles in which the surfactant adheres to the polymer surface, polymerization may be conducted in the presence of the surfactant so as to cause adhesion of the surfactant to the polymer surface. Having said that, it is rather preferable to obtain dry powders of the fluorescent resin particles by washing and drying after the polymerization, and to make the dried powder hydrophilic by adding the surfactant. This process allows a greater amount of surfactant to adhere to the polymer surface more uniformly.

<Tracer Particles>

The fluorescent resin particles according to the present invention can be suitably employed as tracer particles for visualizing a fluid flow. When employed as such tracer particles, the fluorescent resin particles of the present invention can detect and analyze the flow of fluid or air bubble by emission of fluorescence. To serve as the tracer particles, the fluorescent resin particles of the present invention may be added to fluid such as water, either directly by itself or as a dispersion in which the fluorescent resin particles of the present invention are dispersed in a dispersion medium such as water.

<Dispersion>

The dispersion according to the present invention contains the fluorescent resin particles of the present invention. The dispersion of the present invention may be employed not only for tracer particles but also for a coating material. As a dispersion for a coating material, the dispersion of the present invention is advantageous in that the fluorescent resin particles do not settle out in the liquid.

In the dispersion of the present invention, the fluorescent resin particles of the present invention are dispersed as a dispersoid in a dispersion medium. A suitable dispersion medium is an aqueous medium.

The aqueous medium is water, or a mixed medium of water and an organic solvent whose solubility parameter (hereinafter abbreviated as "SP") calculated by Fedor's method is 20.5 $(MPa)^{1/2}$ (10 $(cal/cm^3)^{1/2}$) or more. The specific gravity of the aqueous medium is greater than that of the polymer particles ($\rho_p > \rho_f$). Specific examples of the organic solvent whose SP is 20.5 $(MPa)^{1/2}$ or more include isopropyl alcohol whose SP is 24.3 $(MPa)^{1/2}$ (11.9 $(cal/cm^3)^{1/2}$), methyl alcohol whose SP is 28.2 $(MPa)^{1/2}$ (13.8 $(cal/cm^3)^{1/2}$), ethyl alcohol whose SP is 26.2 $(MPa)^{1/2}$ (12.6 $(cal/cm^3)^{1/2}$), etc.

When employed for a coating material, the dispersion of the present invention usually contains a binder. The fluorescent resin particles as the dispersoid are dispersed in the binder.

The binder is not particularly limited if applicable in the intended field, considering the required characteristics such as transparency, dispersibility of polymer particles, light resistance, humidity resistance, heat resistance, etc. The binder may be a binder resin, examples of which include (meth)acrylic resins; (meth)acrylic-urethane-based resins; urethane-based resins; polyvinyl chloride-based resins; polyvinylidene chloride-based resins; melamine-based resins; styrenic resins; alkyd-based resins; phenolic resins; epoxy-based resins; polyester-based resins; silicone-based resins such as alkyl polysiloxane-based resins; modified silicone resins such as (meth)acrylic-silicone-based resins, silicone-alkyd-based resins, silicone-urethane-based resins, and silicone-polyester resins; fluorine-based resins such as polyvinylidene difluoride, and fluoroolefin vinyl ether polymer; and the like.

For improved durability of the dispersion for a coating material, the binder resin is preferably a curable resin that can form a crosslinked structure by a crosslinking reaction. The curable resin can cure under various curing conditions. Depending on the curing type, curable resins are classified into ionizing radiation curable resins (e.g., ultraviolet curable resins and electron beam curable resins), thermosetting resins, hot air curable resins, etc.

The thermosetting resins include thermosetting urethane resins that contain acrylic polyols and isocyanate prepolymers, phenolic resins, urea melamine resins, epoxy resins, unsaturated polyester resins, silicone resins, etc.

The ionizing radiation curable resins include polyfunctional (meth)acrylate resins such as polyvalent alcohol polyfunctional (meth)acrylates; polyfunctional urethane acrylate resins synthesized from, for example, diisocyanates, polyvalent alcohols, and (meth)acrylic acid esters having a hydroxy group; and the like. Preferable ionizing radiation curable resins are polyfunctional (meth)acrylate resins, of which polyvalent alcohol polyfunctional (meth)acrylates having three or more (meth)acryloyl groups per molecule are more preferable. Specific examples of the polyvalent alcohol polyfunctional (meth)acrylates having three or more (meth)acryloyl groups per molecule are trimethylolpropane tri(meth)acrylate, trimethylolethane tri(meth)acrylate, 1,2,4-cyclohexane tri(meth)acrylate, pentaglycerol triacrylate, pentaerythritol tetra(meth)acrylate, pentaerythritol tri(meth)acrylate, dipentaerythritol triacrylate, dipentaerythritol pentaacrylate, dipentaerythritol tetra(meth)acrylate, dipentaerythritol hexa(meth)acrylate, tripentaerythritol triacrylate, tripentaerythritol hexaacrylate, etc. Two or more of such ionizing radiation curable resins may be used together.

As further examples, the ionizing radiation curable resins may be polyether resins each having an acrylate functional group, polyester resins, epoxy resins, alkyd resins, spiroacetal resins, polybutadiene resins, polythiol-polyene resins, etc.

If the ionizing radiation curable resin is an ultraviolet curable resin, a binder resin contains the ultraviolet curable resin and a photopolymerization initiator added thereto. The photopolymerization initiator is not particularly limited, but is preferably selected in consideration of the ultraviolet curable resin.

Examples of the photopolymerization initiator include acetophenones, benzoins, benzophenones, phosphine oxides, ketals, a-hydroxyalkylphenones, a-aminoalkylphenones, anthraquinones, thioxanthones, azo compounds, peroxides (as disclosed in JP 2001-139663 A, etc.), 2,3-dialkyldione compounds, disulfide compounds, fluoroamine compounds, aromatic sulfoniums, onium salts, borate salts, active halides, a-acyloxime esters, etc.

The acetophenones include, for example, acetophenone, 2,2-diethoxyacetophenone, p-dimethylacetophenone, 1-hydroxydimethylphenyl ketone, 1-hydroxycyclohexylphenyl ketone, 2-methyl-4-methylthio-2-morpholinopropiophenone, 2-benzyl-2-dimethylamino-1-(4-morpholinophenyl)-butanone, etc. The benzoins include, for example, benzoin, benzoin benzoate, benzoin benzene sulfonate ester, benzoin toluensulfonate ester, benzoin methyl ether, benzoin ethyl ether, benzoin isopropyl ether, etc. The benzophenones include, for example, benzophenone, 2,4-dichlorobenzophenone, 4,4'-dichlorobenzophenone, p-chlorobenzophenone, etc. The phosphine oxides include, for example, 2,4,6-trimethylbenzoyl diphenylphosphine oxide, etc. The ketals include, for example, benzyl methyl ketals such as 2,2-dimethoxy-1,2-diphenylethane-1-one. The a-hydroxyalkylphenones include, for example, 1-hydroxycyclohexyl phenyl ketone. The a-aminoalkylphenones include, for example, 2-methyl-1-[4-(methylthio)phenyl]-2-(4-morpholinyl)-1-propanone.

Preferable examples of commercially available photoradical polymerization initiators are sold under the trade names "IRGACURE® 651" (2,2-dimethoxy-1,2-diphenylethane-1-one), "IRGACURE® 184", and "IRGACURE® 907" (2-methyl-1-[4-(methylthio)phenyl]-2-(4-morpholinyl)-1-propanone), all of which are manufactured by BASF Japan Ltd.

The photopolymerization initiator is added usually in the range of 0.5% to 20% by weight, preferably in the range of 1% to 5% by weight, relative to 100% by weight of the binder.

The binder resins are not limited to the above-mentioned curable resins but may also be thermoplastic resins. Such thermoplastic resins include cellulose derivatives such as acetylcellulose, nitrocellulose, cellulose acetate butyrate, ethylcellulose, and methylcellulose; vinyl-based resins such as vinyl acetate homopolymers and copolymers, vinyl chloride homopolymers and copolymers, and vinylidene chloride homopolymers and copolymers; acetal resins such as polyvinyl formal, and polyvinyl butyral; (meth)acrylic resins such as acrylate ester homopolymers and copolymers, and methacrylate ester homopolymers and copolymers; polystyrene resins; polyamide resins; linear polyester resins; polycarbonate resins; and the like.

The binder is not necessarily any of the above-mentioned binder resins but may be any of rubber-based binder resins (e.g., synthetic rubbers and natural rubbers), inorganic binders, and the like. The rubber-based binder resins include ethylene-propylene copolymer rubber, polybutadiene rubber, styrene-butadiene rubber, acrylonitrile-butadiene rubber, etc. These rubber-based binder resins may be used alone or in combination.

The inorganic binder may be silica sol, alkali silicate, silicon alkoxides, phosphoric acid salts, etc. The inorganic binder may also be an inorganic or organic-inorganic composite matrix obtained by hydrolysis and dehydration condensation of a metal alkoxide or a silicon alkoxide. The inorganic or organic-inorganic composite matrix may be a silicon oxide-based matrix obtained by hydrolysis and dehydration condensation of a silicon alkoxide (e.g., tetraethoxysilane). These inorganic binders may be used alone or in combination.

In the dispersion for a coating material, the amount of fluorescent resin particles is preferably 2 parts by weight or more, more preferably 4 parts by weight or more, and further preferably 6 parts by weight or more, relative to 100 parts by weight of the solid content of the binder. When the amount of fluorescent resin particles is 2 parts by weight or more relative to 100 parts by weight of the solid content of the binder, the dispersion for a coating material is more likely to impart sufficient flatting (matting) property to a coating film. Further in the dispersion for a coating material, the amount of fluorescent resin particles is preferably 300 parts by weight or less, more preferably 200 parts by weight or less, and further preferably 100 parts by weight or less, relative to 100 parts by weight of the solid content of the binder. When the amount of fluorescent resin particles is 300 parts by weight or less relative to 100 parts by weight of the solid content of the binder, the dispersion for a coating material is more likely to impart sufficient linear permeability to a coating film.

<Resin Composition>

The resin composition according to the present invention contains the fluorescent resin particles of the present invention and a binder resin. The binder resin may be any of the above-mentioned binder resins for the dispersion for a coating material, and also may be a (meth)acrylic-styrene resin (a copolymer of (meth)acrylic acid ester and styrene), a polycarbonate resin, or the like.

In the resin composition, the amount of fluorescent resin particles is preferably 2 parts by weight or more, more preferably 4 parts by weight or more, and further preferably 6 parts by weight or more, relative to 100 parts by weight of the binder resin. When the amount of fluorescent resin particles is 2 parts by weight or more relative to 100 parts by weight of the binder resin, the resin composition is more likely to have sufficient flatting (matting) property. Further in the resin composition, the amount of fluorescent resin particles is preferably 300 parts by weight or less, more preferably 200 parts by weight or less, and further preferably 100 parts by weight or less, relative to 100 parts by weight of the binder resin. When the amount of fluorescent resin particles is 300 parts by weight or less relative to 100 parts by weight of the binder resin, the resin composition is more likely to have sufficient linear permeability. The resin composition may further contain an additive such as an ultraviolet absorber, an antioxidant, a heat stabilizer, a light stabilizer, a fluorescent brightener, or the like.

The resin composition of the present invention may be formed into a molded product, by various molding methods as described below. For example, if the binder resin is an ultraviolet curable resin, the binder resin is poured into the mold and cured by ultraviolet radiation. As an example, the resin composition may be melt-kneaded with use of a monoaxial extruder, a twin-screw extruder, or the like. As another example, a molding material prepared by melt-kneading of the resin composition may be formed into a plate shape or the like through a T-die and a roll unit. As a further example, a pelletized molding material (master pellets) prepared by melt-kneading and pelletization of the resin composition may be formed into a plate shape by injection molding, press molding, or the like. The size and shape of the molded product can be suitably selected in accordance with its application. If the binder resin in the molded product is a transparent resin, polymer particles in the molded product serve as a light diffusing agent, and allows the molded product to serve as a light diffuser such as a light diffusion plate. Such a molded product can be utilized as an LED lamp cover or the like.

EXAMPLES

Hereinafter, the present invention is described by way of Examples and Comparative Examples, which are not intended to limit the present invention. In following Examples and Comparative Examples, characteristics of the fluorescent resin particles were measured and evaluated by the following methods.

<Method for Measuring the Emulsion Content Index Value of the Fluorescent Resin Particles>

In a 50-ml sample bottle, 10.0 g of the fluorescent resin particles were fed, and 30.0 g of water was added thereto. Using an ultrasonic cleaner ("ULTRASONIC CLEANER VS-150" manufactured by VELVO-CLEAR, oscillation frequency: 50 kHz, high-frequency output:150 W), a dispersion treatment was conducted for 30 minutes to disperse the fluorescent resin particles in the water, thereby giving a dispersion. If the fluorescent resin particles were poorly dispersible in water, the fluorescent resin particles were optionally wetted with a trace (0.8 g at the maximum) of alcohol (e.g., ethanol) before dispersed in water.

The dispersion was then subjected to suction filtration through a filter ("Qualitative Filter Paper No. 101", diameter 55 mm, manufactured by Toyo Roshi Kaisha, Ltd.)". The turbidity of the filtrate was measured and taken as the emulsion content index value. The turbidity was measured with use of a turbidity meter "TurbiDirect" (manufactured by Tintometer).

<Method for Measuring the True Specific Gravity of the Fluorescent Resin Particles>

The density (true specific gravity) of the fluorescent resin particles was measured according to Method A in JIS K5101-11-1, and taken as the true specific gravity of the fluorescent resin particles. Specifically, the true specific gravity was measured in a constant temperature chamber at 20° C. To start with, a 50-ml Wadon type pycnometer was completely filled with ethanol. The mass of the filled pycnometer was weighed and recorded as A (g). Next, ethanol in the pycnometer was removed to drain the pycnometer. To this empty pycnometer, about 3 g of the fluorescent resin particles were supplied as the test sample. The mass of the supplied fluorescent resin particles was weighed and recorded as B (g). To this pycnometer, ethanol was added until the pycnometer was completely filled with the fluorescent resin particles and ethanol. The mass of the filled pycnometer was recorded as C (g). The true specific gravity of the fluorescent resin particles was calculated by the following calculation formula.

True specific gravity (g/ml)= $B \times 0.7950/(A-C+B)$     [Calculation Formula]

<Method for Measuring the Volume-Average Particle Size of the Fluorescent Resin Particles and the Coefficient of Variation in Volume-Based Particle Size>

The volume-average particle size of the fluorescent resin particles and the coefficient of variation (CV) in volume-based particle size were measured by the Coulter technique as described below.

The volume average particle size of the fluorescent resin particles was measured by Coulter Multisizer™ 3 (a measurement device manufactured by Beckman Coulter, Inc.).

For the measurement, the aperture was calibrated according to the user's manual of Multisizer™ 3 issued by Beckman Coulter, Inc.

The aperture for measurement was properly selected in accordance with the size of the fluorescent resin particles to be measured. "Current" (aperture current) and "Gain" (gain) were set in accordance with the selected aperture size. For example, when the 50-μm aperture was selected, "Current" (aperture current) was set to −800, and "Gain" was set to 4.

A measurement sample was prepared as a dispersion in which 0.1 g of the fluorescent resin particles were dispersed in 10 ml of an aqueous solution of a 0.1-wt % non-ionic surfactant, by using a touch mixer ("TOUCHMIXER MT-31" manufactured by Yamato Scientific Co., Ltd.) and an ultrasonic cleaner ("ULTRASONIC CLEANER VS-150" manufactured by VELVO-CLEAR Co., Ltd.). During the measurement, the content in the beaker was gently stirred while avoiding inclusion of air bubbles. The measurement was terminated when 100,000 fluorescent resin particles were measured. The volume average particle size of the fluorescent resin particles was an arithmetic mean of the volume particle size distribution of the 100,000 particles.

For the fluorescent resin particles, the coefficient of variation in volume-based particle size was calculated by the following formula.

Coefficient of variation in volume-based particle size of the fluorescent resin particles=(standard deviation of the volume-based particle size distribution of the fluorescent resin particles/volume-average particle size of the fluorescent resin particles)×100

<Method for Evaluating the Fluorescence-Emitting Property of the Fluorescent Resin Particles>

Fluorescence-emitting property, which is one of the fluid visualization characteristics of the fluorescent resin particles, was evaluated in the following manner. In a 100-ml beaker, 2 g of the fluorescent resin particles were fed, and 50 g of water was added thereto. The fluorescent resin particles were dispersed in the water to give a dispersion. To observe emission of fluorescence, the dispersion was irradiated with blacklight. The fluorescence-emitting property of the fluorescent resin particles was evaluated by visual inspection in three grades: "A" (excellent) means clear emission of fluorescence; "B" (good) means weak emission of fluorescence; and "C" (poor) means no emission of fluorescence.

<Method for Evaluating the Visibility of the Fluid Flow Containing the Fluorescent Resin Particles>

Visibility of the flow of fluid containing the fluorescent resin particles, which is another of the fluid visualization characteristics of the fluorescent resin particles, was evaluated in the following manner. In a 500-ml beaker, 500 ml of distilled water was fed and stirred gently from the bottom of the beaker, using a magnetic stirrer, at a stirring speed of 50 rpm. A 10-mass-percent dispersion of the fluorescent resin particles was added dropwise from the top of the beaker, and the flow of fluid was visually inspected under blacklight. The visibility of the fluid flow was evaluated in three grades: "A" (excellent) means clear confirmation of the fluid flow; "B" (good) means not clear but adequate confirmation of the fluid flow; and "C" (poor) means no confirmation of the fluid flow.

<Method for Overall Evaluation of Fluid Visualization Characteristics of the Fluorescent Resin Particles>

If the fluorescence-emitting property and the visibility of the fluid flow were both "A", the overall evaluation of the fluid visualization characteristics was "A". If either of the fluorescence-emitting property or the visibility of the fluid flow was "B" and the other one was "B" or "A", the overall evaluation of the fluid visualization characteristics was "B". If even one of the fluorescence-emitting property and the visibility of the fluid flow was "C", the overall evaluation of the fluid visualization characteristics was "C".

Example 1

An oil phase was prepared as a mixture of 135 parts by mass of p-tert-butylstyrene (45% by mass in the monomer mixture), as the first vinyl-based monomer; 135 parts by mass of styrene (45% by mass in the monomer mixture), as the specified monofunctional vinyl-based monomer; 15 parts by mass of divinylbenzene (5% by mass in the monomer mixture), as the polyfunctional vinyl-based monomer; 15 parts by mass of 2-methacryloyloxyethyl succinate (5% by mass in the monomer mixture), as the specified monofunctional vinyl-based monomer and the carboxy group-containing monofunctional vinyl-based monomer; 0.3 parts by mass of Rhodamine B, as the water-soluble fluorescent dye; 0.3 parts by mass of caprolactone ethoxylated phosphate dimethacrylate (product name "KAYAMER® PM-21", manufactured by Nippon Kayaku Co., Ltd.), as the acidic modified organophosphate compound; and 3 parts by mass of 2,2'-azobis(2,4-dimethylvaleronitrile) (ABNV) (manufactured by JAPAN FINECHEM COMPANY, INC.) and 0.1 part by mass of benzoyl peroxide, each as the polymerization initiator. An aqueous phase was prepared as a mixture of 700 parts by mass of deionized water, as the aqueous medium; and 7 parts by mass of polyvinyl alcohol (PVA), as the dispersant.

The oil phase and the aqueous phase were mixed to give a suspension. The suspension was fed in a polymerization vessel equipped with a stirrer and a thermometer. For suspension polymerization, the internal temperature of the polymerization vessel was raised to 60° C. (first-stage heating), and the suspension was continuously stirred at a stirring speed of 350 rpm for five hours. To this suspension, 0.05 parts by mass of sodium dodecylbenzene sulfonate was added as the anionic surfactant. Thereafter, the internal temperature of the polymerization vessel was raised to 100° C. (second-stage heating), and the suspension was continuously stirred at 100° C. for three hours to complete the suspension polymerization. The suspension was cooled, and then dehydrated by filtration to separate the solid content. The solid content was washed with sufficient water. The solid content was vacuum dried at 70° C. for 24 hours to give dried powder. To 100 parts by mass of the dried powder, a 0.5-mass-percent aqueous solution of polyoxyethylene sorbitan monolaurate was added in an amount of 20 parts by mass as the non-ionic surfactant. The mixture was dried at 50° C. for 24 hours to give fluorescent resin particles.

Figure 1:
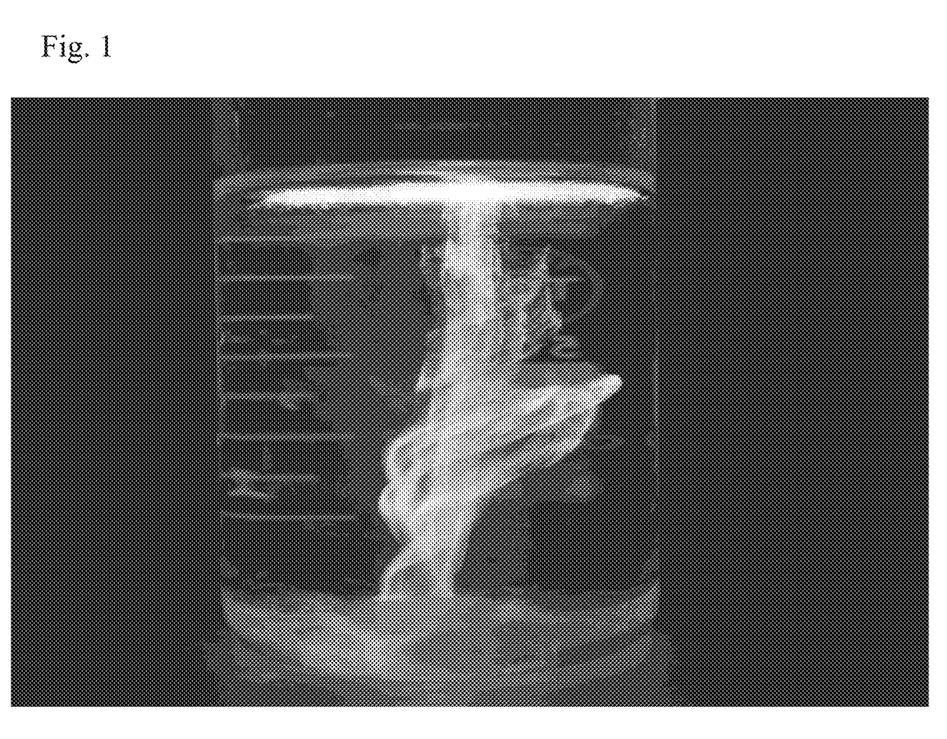
FIG. 1 shows an appearance of fluid containing fluorescent resin particles obtained in Example 1, in visibility evaluation of a fluid flow.

The thus obtained fluorescent resin particles had good fluorescence-emitting property and good visibility. In the visibility evaluation of the flow of fluid containing the fluorescent resin particles according to the above-described method, the fluid flow was observed well as shown in FIG. 1. FIG. 1 shows an appearance of fluid containing the fluorescent resin particles, in the visibility evaluation of the fluid flow.

Example 2

The amount of p-tert-butylstyrene was changed to 150 parts by mass (50% by mass in the monomer mixture), and the amount of styrene was changed to 120 parts by mass (40% by mass in the monomer mixture). The water-soluble fluorescent dye was changed from 0.3 parts by mass of Rhodamine B to 0.15 parts by mass of Rhodamine 640. The stirring speed during the polymerization was changed to 400 rpm. Except these changes, fluorescent resin particles were obtained in the same manner as in Example 1. From the obtained fluorescent resin particles, fine particles were removed with use of an air classifier such that the percentage of fine particles having a particle size of 30 µm or less is 1% by mass or less.

Example 3

This Example did not use 135 parts by mass of styrene. The first vinyl-based monomer was changed from 135 parts by mass of p-tert-butylstyrene to 210 parts by mass of isostearyl acrylate (70% by mass in the monomer mixture). The polyfunctional vinyl-based monomer was changed from 15 parts by mass of divinylbenzene to 60 parts by mass of ethylene glycol dimethacrylate (20% by mass in the monomer mixture). The amount of 2-methacryloyloxyethyl succinate was changed to 30 parts by mass (10% by mass in the monomer mixture). The water-soluble fluorescent dye was changed from 0.3 parts by mass of Rhodamine B to 0.1 part by mass of Rhodamine 640. The stirring speed during the polymerization was changed to 600 rpm. Except these changes, fluorescent resin particles were obtained in the same manner as in Example 1.

Example 4

The amount of styrene was changed to 90 parts by mass (30% by mass in the monomer mixture), and the amount of 2-methacryloyloxyethyl succinate was changed to 60 parts by mass (20% by mass in the monomer mixture). The amount of Rhodamine B was changed to 0.9 parts by mass. The stirring speed during the polymerization was changed to 600 rpm. Except these changes, fluorescent resin particles were obtained in the same manner as in Example 1. From the obtained fluorescent resin particles, fine particles and coarse particles were removed with use of an air classifier such that the percentage of fine particles having a particle size of 10 µm or less and the percentage of coarse particles having a particle size of 60 µm or more were 1% by mass or less each.

Example 5

The first vinyl-based monomer was changed from 135 parts by mass of p-tert-butylstyrene to 135 parts by mass of 4-n-octylstyrene (45% by mass in the monomer mixture). The stirring speed during the polymerization was changed to 300 rpm. Except these changes, fluorescent resin particles were obtained in the same manner as in Example 1.

Example 6

As the carboxylic acid which was free of an ethylenic unsaturated group and whose solubility at 20° C. was 50 g or less per 100 ml water, 15 parts by mass of 2-methacryloyloxyethyl succinate was replaced with 15 parts by mass of octanoic acid (5% by mass in the monomer mixture). The amount of Rhodamine B was changed to 0.1 part by mass. The stirring speed during the polymerization was changed to 400 rpm. Except these changes, fluorescent resin particles were obtained in the same manner as in Example 1.

Example 7

This Example did not use 135 parts by mass of styrene. The first vinyl-based monomer was changed from 135 parts by mass of p-tert-butylstyrene to 215 parts by mass of vinyl stearate (71.7% by mass in the monomer mixture). The polyfunctional vinyl-based monomer was changed from 15 parts by mass of divinylbenzene to 65 parts by mass of ethylene glycol dimethacrylate (21.6% by mass in the monomer mixture). The amount of water-soluble fluorescent dye, Rhodamine B, was changed to 0.1 part by mass. The stirring speed during the polymerization was changed to 600 rpm. Except these changes, fluorescent resin particles were obtained in the same manner as in Example 1. In this Example, the amount of 2-methacryloyloxyethyl succinate was 6.7% by mass in the monomer mixture.

Example 8

This Example did not use 135 parts by mass of styrene. The first vinyl-based monomer was changed from 135 parts by mass of p-tert-butylstyrene to 215 parts by mass of isostearyl acrylate (71.7% by mass in the monomer mixture). The polyfunctional vinyl-based monomer was changed from 15 parts by mass of divinylbenzene to 65 parts by mass of ethylene glycol dimethacrylate (21.7% by mass in the monomer mixture). The water-soluble fluorescent dye was changed from 0.3 parts by mass of Rhodamine B to 0.1 parts by mass of fluorescein. The stirring speed during the polymerization was changed to 600 rpm. Except these changes, fluorescent resin particles were obtained in the same manner as in Example 1. In this Example, the amount of 2-methacryloyloxyethyl succinate was 6.7% by mass in the monomer mixture.

Comparative Example 1

This Comparative Example did not use p-tert-butylstyrene. The amount of styrene was changed to 225 parts by mass (75% by mass in the monomer mixture). The amount of 2-methacryloyloxyethyl succinate was changed to 60 parts by mass (20% by mass in the monomer mixture). The amount of Rhodamine B was changed to 0.9 parts by mass. The stirring speed during the polymerization was changed to 300 rpm. Except these changes, fluorescent resin particles were obtained in the same manner as in Example 1.

Figure 2:
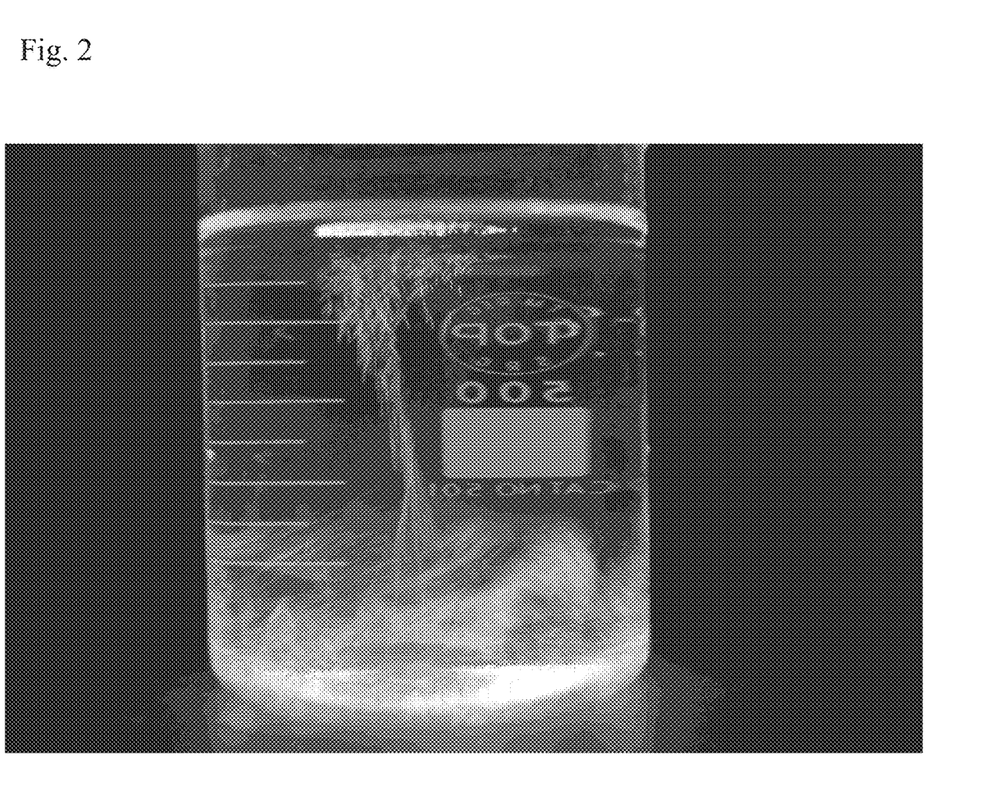
FIG. 2 shows an appearance of fluid containing fluorescent resin particles obtained in Comparative Example 1, in visibility evaluation of a fluid flow.

The thus obtained fluorescent resin particles had good fluorescence-emitting property but poor visibility. In the visibility evaluation of the flow of fluid containing the fluorescent resin particles according to the above-described method, the fluid flow could not be observed as shown in FIG. 2. FIG. 2 shows an appearance of fluid in the visibility evaluation of the fluid flow containing the fluorescent resin particles.

Comparative Example 2

This Comparative Example did not use styrene. The amount of p-tert-butylstyrene was changed to 270 parts by mass (90% by mass in the monomer mixture). The stirring speed during the polymerization was changed to 300 rpm. Except these changes, fluorescent resin particles were obtained in the same manner as in Example 1.

Regarding the fluorescent resin particles obtained in Examples 1 to 8 and Comparative Examples 1 and 2, Table 1 shows measurement results in terms of emulsion content index value (NTU), true specific gravity, volume-average particle size (µm), and coefficient of variation in particle size (%), and also shows evaluation results in terms of fluorescence-emitting property, visibility of fluid flow, and overall evaluation. These results are shown along with the raw materials and their amounts (parts by mass) for the respective fluorescent resin particles.

TABLE 1

|  |  | Examples ||||||||  Comparative Examples ||
|---|---|---|---|---|---|---|---|---|---|---|---|
|  |  | 1 | 2 | 3 | 4 | 5 | 6 | 7 | 8 | 1 | 2 |
| Monomers, etc. | p-tert-butylstyrene | 135 | 150 | — | 135 | — | 135 | — | — | — | 270 |
|  | 4-n-octylstyrene | — | — | — | — | 135 | — | — | — | — | — |
|  | styrene | 135 | 120 | — | 90 | 135 | 135 | — | — | 225 | — |
|  | divinylbenzene | 15 | 15 | — | 15 | 15 | 15 | — | — | 15 | 15 |
|  | 2-methacryloyloxyethyl succinate | 15 | 15 | 30 | 60 | 15 | — | 20 | 20 | 60 | 15 |
|  | octanoic acid | — | — | — | — | — | 15 | — | — | — | — |
|  | isostearyl acrylate | — | — | 210 | — | — | — | — | 215 | — | — |
|  | vinyl stearate | — | — | — | — | — | — | 215 | — | — | — |
|  | ethylene glycol dimethacrylate | — | — | 60 | — | — | — | 65 | 65 | — | — |
| Water-soluble fluorescent dye | Rhodamine B | 0.3 | — | — | 0.9 | 0.3 | 0.1 | 0.1 | — | 0.9 | 0.3 |
|  | Rhodamine 640 | — | 0.15 | 0.1 | — | — | — | — | — | — | — |
|  | fluorescein | — | — | — | — | — | — | — | 0.1 | — | — |
| Properties of fluorescent resin particles | emulsion content index value (turbidity) (NTU) | 13 | 10 | 20 | 30 | 20 | 15 | 20 | 20 | 930 | 15 |
|  | true specific gravity | 1.02 | 1.00 | 1.02 | 1.03 | 1.04 | 1.02 | 1.03 | 1.03 | 1.09 | 0.96 |
|  | volume-average particle size (μm) | 100.7 | 70.3 | 45.3 | 50.8 | 98.4 | 70.7 | 47.5 | 48.3 | 89.5 | 90.4 |
|  | coefficient of variation in particle size (%) | 27.2 | 23.4 | 30.3 | 18.5 | 28.3 | 29.3 | 30.8 | 30.7 | 34.3 | 35.6 |
| Evaluation of fluid visualization characteristics of fluorescent resin particles | fluorescence-emitting property | A | A | B | A | A | A | A | B | B | B |
|  | visibility of fluid flow | B | A | B | A | B | B | B | B | C | C |
|  | overall evaluation | B | A | B | A | B | B | B | B | C | C |

In terms of emulsion content, the fluorescent resin particles that contain a water-soluble fluorescent dye and a polymer made from the monomer mixture containing the specified monofunctional vinyl-based monomer gave the results as shown above and as discussed below. In Comparative Example 1, the monomer mixture did not contain the first vinyl-based monomer, and the resulting fluorescent resin particles showed a high emulsion content index value and a high emulsion content. In Examples 1 to 8, the monomer mixtures contained the first vinyl-based monomers in the range of 45% to 71.7% by mass, and the resulting fluorescent resin particles showed low emulsion content index values and low emulsion contents.

In terms of visibility of a fluid flow, the fluorescent resin particles that contain a water-soluble fluorescent dye and a polymer made from the monomer mixture containing the specified monofunctional vinyl-based monomer gave the results as shown above and as discussed below. In Comparative Examples 1 and 2, the monomer mixtures contained the first vinyl-based monomer at 0% and 90% by mass, respectively, and the resulting fluorescent resin particles showed poor visibility of the fluid flow. In Examples 1 to 8, the monomer mixtures contained the first vinyl-based monomers in the range of 45% to 71.7% by mass, and the resulting fluorescent resin particles showed good visibility of the fluid flow. Two reasons are assumed for good visibility of the fluid flow observed with the fluorescent resin particles obtained in Examples 1 to 8. For one, the compositions of the fluorescent resin particles obtained in Examples 1 to 8 were likely to allow the fluorescent resin particles to follow the fluid flow better. For another, the emulsion contents were low in the fluorescent resin particles obtained in Examples 1 to 8, which prevented separation of microparticles (emulsion) from the surfaces of the fluorescent resin particles and prevented blurring of an image of the fluid flow derived from the fluorescent resin particles in the intended particle size.

Example 9

Using an agitation defoaming apparatus, 2 parts by weight of the fluorescent resin particles obtained in Example 3, and 20 parts by weight of an aqueous binder dispersion (a commercial acrylic water-based gloss coating material, trade name "Super Hit" manufactured by Kanpe Hapio Co., Ltd.) were mixed for three minutes and defoamed for one minute to give a dispersion.

This dispersion was applied to an ABS resin (acrylonitrile-butadiene-styrene resin) plate, using a coater equipped with a blade (clearance 100 μm), and dried to give a coating film. When irradiated with blacklight, the coating film developed a fluorescent color.

Example 10

Using an agitation defoaming apparatus, 2 parts by weight of the fluorescent resin particles obtained in Example 3, 20 parts by weight of a light curable monomer (dipentaerythritol hexaacrylate, A-DPH, manufactured by Shin-Nakamura Chemical Co., Ltd.) as one of the ultraviolet curable resins, and 0.15 g of a photopolymerization initiator (2-hydroxy-2-methyl-1-phenyl-propane-1-one, product name "IRGACURE® 1173" manufactured by BASF Japan Ltd.) were mixed for three minutes and defoamed for one minute to give a liquid resin composition in which the fluorescent resin particles were uniformly dispersed.

Using a 3-cm-diameter petri dish as a mold, the liquid resin composition was poured in a thickness of 3 mm. The liquid resin composition was cured under ultraviolet radiation to give a molded product of the resin composition containing the fluorescent resin particles. The fluorescent resin particles were uniformly dispersed in this molded product of the resin composition. When irradiated with blacklight, the molded product of the resin composition developed a fluorescent color uniformly.

The invention claimed is:
1. Fluorescent resin particles which comprise a water-soluble fluorescent dye and a polymer made from a monomer mixture, the monomer mixture being a mixture of 20% to 80% by mass of a first vinyl-based monomer and 80% to 20% by mass of a second vinyl-based monomer, the first vinyl-based monomer being at least one monofunctional vinyl-based monomer selected from the group consisting of a styrene derivative having an alkyl group with 3 to 30 carbon atoms, a (meth)acrylic acid ester having an alkyl group with 10 to 30 carbon atoms, and a vinyl ester having an alkyl group with 10 to 30 carbon atoms, and the second vinyl-based monomer comprising at least one monofunctional vinyl-based monomer selected from the group consisting of styrene, a styrene derivative having an alkyl group with two carbon atoms or less, a (meth)acrylic acid ester having an alkyl group with nine carbon atoms or less, and a vinyl ester having an alkyl group with nine carbon atoms or less.

2. The fluorescent resin particles according to claim 1, wherein the second vinyl-based monomer comprises a monofunctional vinyl-based monomer which has a carboxy group and whose solubility at 20° C. is 50 g or less per 100 ml water.

3. The fluorescent resin particles according to claim 1, further comprising a carboxylic acid which is free of an ethylenic unsaturated group and whose solubility at 20° C. is 50 g or less per 100 ml water.

4. The fluorescent resin particles according to claim 1, wherein an emulsion content index value for the fluorescent resin particles is 100 NTU or less, measured as a turbidity of a filtrate of a dispersion in which the fluorescent resin particles are dispersed in water, with the proviso that an amount of water is three times as much as a mass of the fluorescent resin particles, and that the dispersion is filtered through "Qualitative Filter Paper No. 101", manufactured by Toyo Roshi Kaisha, Ltd., to give the filtrate.

5. The fluorescent resin particles according to claim 1, wherein the fluorescent resin particles have a volume-average particle size of 30 to 500 μm.

6. The fluorescent resin particles according to claim 1, wherein a coefficient of variation in volume-based particle size of the fluorescent resin particles is 25% or less.

7. The fluorescent resin particles according to claim 1, further comprising a surfactant.

8. The fluorescent resin particles according to claim 1, wherein a true specific gravity of the fluorescent resin particles is from 0.95 to 1.05.

9. The fluorescent resin particles according to claim 1, wherein the water-soluble fluorescent dye is a rhodamine dye or a fluorescein dye.

10. The fluorescent resin particles according to claim 1, wherein the fluorescent resin particles are tracer particles for visualizing a flow of fluid.

11. A dispersion comprising the fluorescent resin particles according to claim 1.

12. A resin composition comprising the fluorescent resin particles according to claim 1 and a binder resin.

* * * * *